United States Patent
Dreher et al.

(10) Patent No.: US 9,056,083 B2
(45) Date of Patent: Jun. 16, 2015

(54) POMEGRANATE FRUIT POLYPHENOL COMPOSITION AND METHODS OF USE AND MANUFACTURE THEREOF

(75) Inventors: Mark Dreher, Wimberley, TX (US); Harley Liker, Los Angeles, CA (US); Yair Steve Henig, Beverly Hills, CA (US)

(73) Assignee: POM Wonderful, LLC, Los Angeles, CA (US)

( * ) Notice: Subject to any disclaimer, the term of this patent is extended or adjusted under 35 U.S.C. 154(b) by 202 days.

(21) Appl. No.: 13/299,356

(22) Filed: Nov. 17, 2011

(65) Prior Publication Data

US 2012/0269887 A1  Oct. 25, 2012

Related U.S. Application Data

(63) Continuation-in-part of application No. 12/564,878, filed on Sep. 22, 2009, now Pat. No. 8,658,220, which is a continuation of application No. 11/137,248, filed on May 24, 2005, now Pat. No. 7,611,738, application No. 13/299,356, which is a continuation-in-part of application No. 11/745,440, filed on May 7, 2007, now Pat. No. 8,758,832, and a continuation-in-part of application No. 11/687,480, filed on Mar. 16, 2007, now Pat. No. 7,943,185.

(60) Provisional application No. 60/888,763, filed on Feb. 7, 2007, provisional application No. 60/888,762, filed on Feb. 7, 2007.

(51) Int. Cl.
*A61K 36/185* (2006.01)
*A61K 31/7048* (2006.01)

(52) U.S. Cl.
CPC ........... *A61K 36/185* (2013.01); *A61K 31/7048* (2013.01)

(58) Field of Classification Search
CPC .................................................. A61K 2300/00
USPC ........................................................ 424/725
See application file for complete search history.

(56) References Cited

U.S. PATENT DOCUMENTS

2003/0091690 A1*  5/2003  Somoto et al. .................. 426/39

OTHER PUBLICATIONS

Viable Herbal Solutions (www.web.archive.org/web/20000124113842/http:/viable-herbal.com/herbology1/herbs42.htm., copyrighted 1996,1997,1998 and 2000).*

* cited by examiner

*Primary Examiner* — Chris R Tate
*Assistant Examiner* — Randall Winston
(74) *Attorney, Agent, or Firm* — Cotman IP Law group, PLC

(57) ABSTRACT

A pharmaceutical composition with an active pharmaceutical ingredient including a pomegranate fruit polyphenol extract. The pomegranate fruit polyphenol extract includes at least about 3% combined punicalagin A and punicalagin B by weight, less than about 5% ellagic acid and their derivatives by weight, and less than about 1% anthocyanins by weight.

16 Claims, No Drawings

POMEGRANATE FRUIT POLYPHENOL COMPOSITION AND METHODS OF USE AND MANUFACTURE THEREOF

The present application is a continuation-in-part of U.S. patent application Ser. No. 12/564,878, filed on Sep. 22, 2009 now U.S. Pat. No. 8,658,220, which is a continuation application of U.S. patent application Ser. No. 11/137,248, filed on May 24, 2005, now issued as U.S. Pat. No. 7,611,738, all of which are herein incorporated by reference for completeness of disclosure; the present application is also a continuation-in-part of U.S. patent application Ser. No. 11/745,440, filed on May 7, 2007 U.S. Pat. No. 8,758,832, which claims priority to U.S. Provisional Application Ser. No. 60/888,763, and U.S. Provisional Application Ser. No. 60/888,762, both filed Feb. 7, 2007, and which is a continuation-in-part of U.S. patent application Ser. No. 11/687,480 filed on Mar. 16, 2007, now issued as U.S. Pat. No. 7,943,185, all of which are herein incorporated by reference for completeness of disclosure.

BACKGROUND OF THE INVENTION

1. Field of the Invention

The disclosure provided herein relates generally to pomegranate extracts. More particularly, but not by way of limitation, one or more embodiments enable oral or enteral dosage forms containing phytochemicals from pomegranate in a quantity reflecting that of the natural fruit itself.

2. Description of the Related Art

The pomegranate is acclaimed for its health benefits and for its disease-fighting antioxidant potential. Antioxidants are important because they are believed to protect the body against free radicals, the harmful molecules that can cause heart disease, premature aging, Alzheimer's disease, blindness, and a variety of cancers.

There are many kinds of antioxidants, some produced by the body and others derived from the foods we eat. When the body's natural antioxidant defenses are lowered, or greater amounts of free radicals are produced, the body becomes more dependent upon food sources of antioxidants. The consumption of phytochemical-rich diet is associated with a reduced risk of chronic human illnesses such as certain types of cancers, inflammation, and cardiovascular and neurodegenerative diseases.

Studies show pomegranate juice has more polyphenol antioxidants than any other drink, such as red wine, green tea, blueberry juice, cranberry juice and orange juice. Two common ways of consuming pomegranates are by eating the fleshy arils of the pomegranate fruit itself and by drinking the juice obtained from the arils.

There are studies illustrating the beneficial effects of pomegranate phytochemicals, including polyphenols, proanthocyanidins, hydrolysable tannins, etc. Hence it is desirable to gain whatever beneficial effects might be present by consuming pomegranate and its phytochemicals. The oral route is the least invasive, most convenient route for administering pomegranate phytochemicals on a routine basis. However, the pomegranate fruit is a difficult fruit to consume and certain pomegranate phytochemicals may lose their health beneficial effects by undergoing chemical reactions into less bioavailable and/or less bioactive forms during processing and storage of juices and extracts.

For example, a major polyphenol antioxidant called punicalagin can by hydrolyzed into ellagic acid. Once punicalagin hydrolyzes into ellagic acid its ability to offer antioxidant potency to the body is reduced since free ellagic acid is not as bioavailable. When punicalagins are preserved in their original unhdrolyzed and then consumed, they can be absorbed into the bloodstream, and greater health benefits can be obtained. Punicalagins are 100% water-soluble, highly bioavailable, and shown to possess a high absorption rate up to 95%. Not only do punicalagins offer antioxidant activity on their own, they can break up into smaller polyphenols that are also absorbed into the body. Punicalagins are one important component of pomegranate polyphenols, but the total composition of the polyphenols themselves is a complex mixture of numerous other components.

Predominant types of pomegranate polyphenolic compounds are hydrolyzable tannins, which are found in the peels (rind, husk, or pericarp), membranes, and piths of the fruit. Hydrolyzable tannins, including punicalagin, are susceptible to enzymatic and non-enzymatic hydrolysis. Other hydrolyzable tannins are include gallic acid and ellagic acid esters of core molecules that consist of polyols, such as sugars. During hydrolysis, gallotannins yield gallic acid and glucose while ellagitannins yield ellagic acid and glucose. The reported soluble polyphenol content in pomegranate juice varies within the limits of approximately 0.2% to approximately 1.5%, and ellagic acid was measured in commercial juices around 100 to around 3000 mg/L.

For the reasons above, many of products claiming to contain "natural pomegranate" may in fact have less concentrated key ingredients or phytochemicals that have specific health benefits. Hence there is a need to find ways to concentrate pomegranate phytochemicals, including polyphenol antioxidants such as punicalagins and its automers, in their bioavailable and bioactive.

For the reasons above, many of products claiming to contain "natural pomegranate" may in fact lack key ingredients or phytochemicals that have specific health benefits. Hence there is a need to find ways to concentrate pomegranate phytochemicals, including polyphenol antioxidants such as punicalagins and its automers, in their bioavailable and bioactive forms.

For at least the reasons described above there is a need for processes for producing an oral or enteral dosage form containing key phytochemicals from pomegranates.

SUMMARY OF THE INVENTION

One or more embodiments of the pomegranate fruit polyphenol extract described herein are directed to a pharmaceutical composition including an active pharmaceutical ingredient. The active pharmaceutical ingredient includes a pomegranate fruit polyphenol extract including at least about 3% combined punicalagin A and punicalagin B by weight, and less than about 5% ellagic acid and their derivatives by weight, and less than about 1% anthocyanins by weight.

The pharmaceutical composition further includes a pharmaceutically acceptable carrier in instances where a carrier is desired.

In one or more embodiments of the pharmaceutical composition, the pomegranate fruit polyphenol extract may include between about 3% to about 8% combined punicalagin A and punicalagin B by weight. For example, the pomegranate fruit polyphenol extract may include between about 3% to about 4% combined punicalagin A and punicalagin B by weight. In another instance, the pomegranate fruite polyphenol extract may contain between about 4.5% to about 8% combined punicalagin A and punicalagin B by weight. In one or more embodiments, the pomegranate fruit polyphenol extract includes at least about 20% combined punicalagin A and punicalagin B by weight.

In one or more embodiments of the pharmaceutical composition, the pomegranate fruit polyphenol extract includes at least about 15% combined punicalagin and punicalin by weight. The pomegranate fruit polyphenol extract may include at least about 20% combined punicalagin and punicalin by weight. Furthermore, one or more embodiments may include at least about 25% combined punicalagin and punicalin by weight.

The pomegranate fruit polyphenol extract may include less than about 4% ellagic acid and their derivatives by weight.

In one or more embodiments of the pharmaceutical composition, the pomegranate fruit polyphenol extract is formulated to include less than about 3.5% free ellagic acid by weight. Furthermore, pomegranate fruit polyphenol extract may be formulated to include less than about 1.5% free ellagic acid by weight. In one or more embodiments, the pomegranate fruit polyphenol extract includes less than about 0.3% free ellagic acid by weight.

In one or more embodiments of the pharmaceutical composition, the pomegranate fruit polyphenol extract includes less than about 0.1% anthocyanins by weight.

In one or more embodiments, the pomegranate fruit polyphenol extract is obtained from pomegranates of the Wonderful variety but other varietals of pomegranate fruit may be equally sufficient. The pomegranate fruit polyphenol extract may be obtained from pomegranate solids including one or more of the pericarp, inner membrane, and seeds.

The pomegranate fruit polyphenol extract can be delivered in various forms and in at least one embodiment includes at least about 1000 mg of a dry composition containing at least about 80% total polyphenols, at least about 85% total polyphenols, or at least 90% total polyphenols.

The pharmaceutical composition can be administered in various forms may, for example, be selected from an intermediate release composition, a delayed release composition, an extended release composition, a mixed release composition and an enterically coated composition. The pharmaceutical composition may be administered in a capsule or other dosage forms such as a tablet, including but not limited to a bilayer tablet. The pharmaceutical composition can also be administered orally, intramuscularly, intravenously, transdermally, buccally or topically.

DETAILED DESCRIPTION

A pomegranate fruit polyphenol extract will now be described. In the following exemplary description, numerous specific details are set forth in order to provide a more thorough understanding of the embodiments described throughout this disclosure. It will be apparent, however, to an artisan of ordinary skill in the art that the present invention may be practiced without incorporating all aspects of the specific details described herein. In other instances, specific features, quantities, methods, or measurements well known to those of ordinary skill in the art have not been described in detail so as not to obscure the invention. Readers should note that although examples of the invention are set forth herein, the claims, and the full scope of any equivalents, are what define the scope of the invention.

As used herein, the term "phytochemicals" refers collectively to compounds which are naturally-occurring in the pomegranate and to reaction products and metabolites of these compounds, which are considered to have a beneficial effect on the human or animal health. Examples of such phytochemicals include, but are not limited to phenolics, polyphenols, and phenolic acids, sterols and triterpenoids, fatty acids and triglycerides, and alkaloids.

As used herein, the term "polyphenols" refers generally to a family of naturally-occurring compounds in the pomegranate and includes phenols and polyphenols. Phenols are a class of chemical compounds consisting of a single phenol unit in their structure. Although similar to alcohols, phenols have unique properties including relatively higher acidities due to the aromatic ring tightly coupled to the oxygen and a relatively loose bond between the oxygen and the hydrogen. Examples of phenolic compounds within this group include ellagic acid and gallic acid. Polyphenols are a group of compounds, characterized by the presence of more than one phenolic group. Polyphenols include tannins (e.g., ellagitannins and gallotannins), flavonoids (e.g., anthocyanins and isoflavones) and stilbenes (e.g., resveratrol).

As used herein, the term "pomegranate juice" refers to the juice that is substantially obtained from the arils of the pomegranate.

As used herein, the term "pomegranate solids" refers to any one or a combination of the pericarp, the inner membrane and seeds of a pomegranate.

The pomegranate fruit polyphenol extracts described herein are formulated for pharmaceutical or nutriceutical purposes and highly bio-available. In one or more embodiments, such pomegranate fruit polyphenol extracts comprise a significantly higher total polyphenol content, particularly of the high molecular weight polyphenol (e.g., punicalagin), than is found in pomegranate juice. The pomegranate fruit polyphenol extracts can be administered in various forms and may be mixed with food products, beverages and/or pharmaceutical compositions that complement or increase the effectiveness of the pomegranate fruit polyphenol extract.

One or more embodiments of pomegranate fruit polyphenol extracts are included in a pharmaceutical composition. Such pharmaceutical compositions may be in form of tablets, suspensions, implants, solutions, emulsions, capsules, powders, syrups, liquid compositions, ointments, lotions, creams, pastes, and gels. Such pharmaceutical compositions may also be in form of pharmaceutical preparations, nutritional supplements, vitamin supplements, food additives, and food supplements.

The pomegranate fruit polyphenol extracts may also be included in a pharmaceutical composition along with one or more pharmaceutically suitable carriers. Suitable carriers or excipients are inert ingredients and can be included in the composition. Excipients can include, but are not limited to, fillers sugar alcohols, starch, lubricants, and binders. Examples of sugars include lactose, glucose, and sucrose. Sugar alcohols include mannitol, sorbitol, and xylitol. Examples of starch include wheat, corn, or potato starch, modified starch and sodium starch glycolate. Lubricants include talc, magnesium stearate, calcium stearate, colloidal silica, and stearic acid. Binders include polyvinylpyrrolidone, cellulose derivatives, carboxymethyl cellulose, hydroxylpropyl cellulose, hydroxypropylmethyl cellulose, methyl cellulose, and gelatin. Conventional procedures for preparing such compositions in appropriate, dosage forms of the extract may be utilized. Such compositions may be administered orally or parenterally employing liquid form preparations containing the extract. The compositions may be administered orally, in appropriate dosage units of the extract in a pharmaceutically acceptable carrier or excipient. Thus, the compositions may be formulated into solid or liquid preparations, such as capsules, pills, tablets, powders, solutions, suspension, or emulsions and prepared according to methods known in the art for the manufacture of such compositions. The solid unit dosage forms may be in form of a hard or soft shelled gelatin capsule containing the extract and a suitable carrier or excipient.

The composition may also be administered parenterally as injectable dosages in a physiologically acceptable carrier. Parenteral administration may be subcutaneous, intravenous, intramuscular, or interperitoneally.

One or more embodiments of compositions containing the extract and the pomegranate juice are provided. The combination of the extract and pomegranate juice not only produces a composition having a higher total polyphenol content, as compared to the pomegranate juice alone, but it also provides the broad spectrum of the different polyphenols which predominate the pomegranate juice and extract. The pomegranate fruit polyphenol extracts are provided for preventing or ameliorating disease conditions in a subject by administering to the subject an effective amount of the composition suitable for use in pharmaceutical composition or nutritional preparation. Such disease conditions include polyphenol-mediated diseases and cancer. Examples of polyphenol-mediated diseases include circulatory disorders such as hypertension and coronary artery disease, erectile dysfunction, lung disorders such as asthma, cancers of various types, inflammatory conditions, certain liver conditions, diabetes, mood disorders, eye disorders such as cataracts, weak eyesight due to aging, macular degeneration, and other age-related disorders, such as Alzheimer's disease and dementia.

Examples of methods are provided for modulating the growth and progression of cancerous cells, the methods comprising selecting a subject having cancerous cell growth and administering to the subject an effective amount of the composition containing the extract. One or more embodiments described are provided for preventing or slowing increases in the Prostate Specific Antigen (PSA) levels in a subject having prostate cancer. An effective amount of a pharmaceutical composition comprising pomegranate fruit polyphenol extracts is administered to a subject having prostate cancer.

One or more embodiments of pharmaceutical compositions including the pomegranate fruit polyphenol extracts described herein include an effective amount of pomegranate fruit polyphenol extract sufficient to achieve the intended beneficial health results. Accordingly, the effective amount of the composition to be administered depends on considerations such as the dosage unit employed, the mode of administration, the period of treatment, the age, sex and weight of the person treated and the nature and extent of the condition treated. The effective amount can readily be determined based upon standard techniques known to evaluate whether the intended effect of the composition has been achieved, by standard toxicity tests and by standard pharmacological assays.

Pomegranate Polyphenols

Turning to pomegranate extracts, it was been surprisingly discovered that extracts obtained from the pomegranate solids, in accordance with the methods disclosed herein, have substantially higher total polyphenol content than is found in the juice from the pomegranate arils. This is particularly true with respect to the higher molecular weight polyphenols (e.g., punicalagin).

Punicalagin is a powerful antioxidant, which is found in at least two isoforms (punicalagin-α and punicalagin-β). Two features of punicalagins relate to the protection of cardiovascular function and accurate cellular replication. Thus, the punicalagin automers are responsible, in part, for the high antioxidant activity of the extract. While the antioxidant and other beneficial health effects of the extract are due to the presence of polyphenols, the presence of other phytochemical compounds in the extract, or the synergistic effect of these phytochemicals, can also be responsible for the antioxidant and other beneficial health effects of the extract.

In addition to punicalagin, other high molecular weight polyphenols have been characterized in the extract of pomegranate solids. These high molecular weight polyphenols include ellagitannin and other hydrolysable tannins, such as punicacortein A, punicalin, pedunculagin, and gallotanin dimers and trimers. The pomegranate extract in the administered composition can be between about 20% to about 40% by HPLC area of a combination of punicalin and punicalagin; and between about 1% to about 5% by HPLC area of ellagic acid. In one or more embodiments, the punicalagin includes the automers punicalagin-α and punicalagin-β. composition can also comprise other pomegranate polyphenol compounds, including, but not limited to, gallic acid, an isoflavone (e.g., genistein or daidzein, as well as methylated pr glycoside derivatives thereof), an anthocyanin, a hydrolyzable tannin, and/or combinations thereof.

Moreover, a large number of anthocyanins have been characterized in the extract of the pomegranate solids. Examples of the anthocyanins include pelargonidin 3-glucoside, cyaniding 3-glucoside, delphinidin 3-glucoside, pelargonidin 3,5-diglucoside, cyaniding 3,5-diglucoside, and delphinidin 3,5-diglucoside. Although these anthocyanins have been characterized in both the pomegranate juice and the extract, these lower molecular weight polyphenols comprise a higher proportion of the total polyphenol content in pomegranate juice (approximately 50%) than in the extract.

Pomegranate Fruit Polyphenol Extracts and Extraction Methods

The pomegranate fruit polyphenol extracts are obtained from at least one pomegranate solid. For instance, one may make use of the pericarp, inner membrane and seeds to create a mixture comprising the pomegranate solids in an aqueous solution. In one or more embodiments, the mixture of the pomegranate solids may be created by adding water in an amount that is about 20 to about 80% w/v, and more preferably about 50% w/v, of the pomegranate solids. The mixture is preferably crushed or milled to create a rough grind of pomegranate solids dispersed in the aqueous solution.

In other instances the starting materials for production of the pomegranate fruit polyphenol extract are solids from the husks and residual fruits remaining after the first or second pressing of whole fruits in the production of the juice concentrate. Both powder or concentrated liquid forms may be made with these materials. In one or more embodiments, the mixture of the solids may be created by adding water in an amount that is about 20 to about 80% w/v, and more preferably about 50 w/v, of the solids. The mixture may be crushed or milled to create a rough grind of pomegranate solids dispersed in the aqueous solution.

The extracts obtained from pomegranate solids with a substantially higher total polyphenol content than is found in the juice from the pomegranate arils. This is particularly true with respect to the higher molecular weight polyphenols and, in particular, punicalagin.

In one or more embodiments, the pomegranate fruit polyphenol extract is produced by providing pomegranate solids selected from the group consisting of the pericarp, inner membrane and seeds and creating a mixture comprising the pomegranate solids in an aqueous solution. In an exemplary embodiment, the mixture of the pomegranate solids is created by adding water in an amount that is about 20 to about 80% w/v, and more preferably about 50% w/v, of the pomegranate solids. The mixture is preferably crushed or milled to create a rough grind of pomegranate solids dispersed in the aqueous solution. The mixture is then heated to a temperature of about 60° F. to about 210° F., about 85° F. to about 185° F., or about 110° F. to about 160° F. The temperature to which the mixture is heated depends upon the selection of enzymes, or combination of enzymes, added to the mixture. In one or more embodiments, the mixture is heated to a temperature that permits the maximum catalysis of the enzyme or combination of enzymes. Enzymes may also be added before the mixture is heated. Thus, the order of the steps of heating the mixture and adding the enzymes is not critical, so long as the mixture is heated to a temperature that permits the enzymes to at least partially degrade the pomegranate solids and liberate phytochemicals from the plant tissues and/or cells. Once liberated, the phytochemicals may react and/or polymerize to create new phytochemical compounds or reaction products. In one or more embodiments, anthocyanins are degraded during the treatment process.

Enzymes suitable for use in accordance with this embodiment include those capable of at least partially degrading the plant tissue or cells to liberate the phytochemicals from the pomegranate solids. Such enzymes include any one or a combination of pectinase, cellulase, hemicellulase, amylase, arabanase, and other hydrolyzing enzymes, to name a few. The enzymes added to the mixture may be naturally-occurring or synthetic. They may be derived from any one or a combination of sources, such as animal, plant, fungal, and bacterial sources. The amount of the enzyme or combination of enzymes added to the mixture depends on the temperature of the mixture and the amount of pomegranate solids present in the mixture. After the enzymes have at least partially degraded the pomegranate solids, the residual insoluble solid materials, such as proteins, are removed from the mixture. Optionally, a clarification agent, such as bentonite, may be added before the step of removing the residual insoluble materials from the mixture. The removal of residual insoluble materials from the mixture may be accomplished by filtration, centrifugation, chromatographic techniques, and other techniques. In another embodiment of the invention the mixture of pomegranate solids is heated to liberate the polyphenols and enzymes are not utilized.

The pomegranate fruit polyphenol extract may be produced by micro-filtration. In one or more embodiments, a molecular weight cut-off of at least 1,000 Da is used. Alternatively, a molecular weight cut-off of between about 4,500 Da to about 5,500 Da is used. In one or more embodiments, micro-filtration is performed using a membrane filter rated for up to about 1 μm. The resulting liquid extract may be concentrated in an evaporator under vacuum to about 50 to u about 90 Brix (Bx), preferably to about 60 to about 80 Bx, and more preferably to about 70 Bx, more preferably to about 65 Bx to about 70 Bx. The extract can then be and pasteurized at a temperature and for a length of time sufficient to kill microorganisms that could cause disease, spoilage or undesired fermentation. In one preferred embodiment, the extract may be pasteurized at a temperature of about 140° F.-280° F., preferably of about 195° F.-240° F., and optimally of about 205° F. The pasteurization may also denature the remaining enzymes that were added to the mixture.

Polyphenols are recovered from the extract concentrate using FDA food-grade resins. Extract concentrate, diluted with water, is passed through resin columns which preferentially adsorbs polyphenols from the extract liquid. The resins do not chemically modify the polyphenols; they reversibly adsorb and desorb the polyphenols with their original chemical structure remaining unchanged. Non-phenol compounds, such as sugars, organic acids, cellulose, and other carbohydrates, pass unadsorbed through the resin column.

Polyphenols adsorbed on the resin are recovered (de-adsorbed) by elution using ethanol in water. In one or more embodiments, the recovered polyphenols include substantially less anthocyanins than the extract liquid, at least partially due to loss during adsorption and/or elution. The recovered polyphenols are concentrated by completely removing ethanol. The remaining polyphenol water solution is dried to produce a pomegranate food polyphenol extract powder. The separation medium may include a synthetic polymeric adsorbent resin. Generally these synthetic polymeric adsorbents take the form of non-ionic macroreticular resins that adsorb and release ionic and polar molecules (compounds) through hydrophobic and polar interactions; these are usually employed under isocratic conditions (i.e., only a single eluent of fixed composition is used). Such polymeric resins are usually derived from a synthetic hydrophobic polyaromatic resin such as cross-linked polyvinylbenzene (polystyrene) and polydivinylbenzene. These resins are manufactured under trade names such as Amberchrom™, Amberlite™, Diaion™, and Dowex™. One advantage of the polystyrene-divinylbenzene copolymer resin is the polyphenols are especially well adsorbed when dissolved in water or dilute aqueous C1-C3 alkanol (e.g. 2% v/v ethanol), preferably at the nominal operating range of 100° to 140° F. It may be possible to use natural polymeric media, such as microparticulate cellulose which is particularly well suited for the separation of nucleotides, sugars, amino acids and polyphenols. Potential drawbacks to the use of microparticulate cellulose or derivatives thereof, are swelling in an aqueous environment and/or compressibility under pressure. Other alternatives are dextran polymers (e.g. Sephadex™, Pharmacia UK) or agarose beads (e.g., Sepharose™, Pharmacia, UK). In one or more embodiments, temperature range for operating the separation process is in the range of 100° to 140° F. Less preferred is using the separation medium at the temperature below 100° F. which alters the adsorption characteristics of polyphenols and other phytochemicals of interest. In one or more embodiments, the flow rate through the separation medium is in the range one to three bed volumes an hour, optimally two bed volumes per hour. A bed volume is the amount of the adsorbent resin in a separation medium. The volume and total time of flow of a particular feed stream into the column can be controlled by the desired output and the input stream. The optimal flow rate enables the separation medium to sequester polyphenols and other phytochemicals of interest, and rinse out the unbound material.

For the rinsing step in one or more embodiments, a dilute aqueous alcohol is passed through the separation medium to remove unbound material (e.g., sugars, proteins, fibers, enzymes, carbohydrates). When obtaining a high purity of polyphenols in the pomegranate dry composition is desired, it is preferred that this rinsing step be performed prior to the elution of polyphenols. Optionally, the rinse step may include back flushing the separation medium with a dilute aqueous alcohol to remove any insoluble material that may collect on the top of the separation medium. Dilute aqueous alcohol is any aqueous solution containing alkanol having one to four carbon atoms and of less than about 5% v/v, more preferable 2% v/v. Ethanol is the preferred alkanol since it is approved for food use, although other alkanols may suffice. Less preferable is water, which is not as effective at getting unbound material out of the separation medium and reduces the purity of polyphenols in the pomegranate dry composition.

In one or more embodiments which is described herein for purposes of example, the pomegranate fruit polyphenol extract is produced by obtaining pomegranate solids, which generally comprise the pericarp, the inner membrane and seed of the pomegranate. In one or more exemplary embodiments, the pomegranate solids are obtained and collected after the primary juice from the arils is substantially expelled or otherwise removed from the pomegranate by pressing, crushing, or other methods known to the art for extracting pomegranate juice. The pomegranate solids are then transferred to three Reitz mills (such as those sold by Reitz Mills) with 3/8 inch screens. The pomegranate solids are milled to a fine puree and heated to approximately 125° F. This step, coupled with the following enzyme addition, assists in breaking down the colloidal structure of the remaining pomegranate solids, thereby releasing the remaining soluble solids. The mixture is heated to a temperature of about 125° F. for two hours. In one or more of the exemplary embodiments described here three enzymes are added to the mixture: pectinase (Rohapect® DA6L), cellulase/pectinase (Rohapect® CL), and hemi-cellulase/pectinase (Rohapect® B1L). These enzymes liberate the remaining pomegranate soluble solids, such as sugars, minerals, anthocyanins, and remaining polyphenols. The mixture is then pumped from the extraction plant to the primary processing plant where it is held in mash treatment tanks for approximately one hour. After one hour, 50-100 pounds of bentonite in a 125 gallon water slurry, per 8,000 gallons of the mixture, is added for protein removal. The treated mixture was then passed through a Westphalia 755 Decanter for removal of solids. The residual insoluble material is typically discharged as waste. The liquid extract then exits the decanter and is filtered on on microfiltration membranes (such as one sold by Koch SUPER-COR®) at a 500,000 Da molecular weight cut-off and then filtered again on Koch ultrafiltration membranes at a 100,000 or 200,000 Da molecular weight cut-off. In one or more embodiments, the filtered liquid extract is optionally applied to a rising-film plate evaporator (such as that sold by Schmidt-Bretten. Initial heat on this step is about 140° F. In this step, the filtered liquid extract is concentrated to about 15° to 20° Bx. The filtered liquid extract is maintained at the temperature of about 140° F. and then passed through a pre-heated preparative column at about 140° F. (4-foot diameter, 4-foot tall) packed with Amberlite™ FPX66 (Rohm and Haas, Philadelphia, Pa.) at the flow rate of about two bed volumes an hour until the resins gets loaded. Any portions of liquid effluent indicating a bleed-through of polyphenols may be collected for subsequent loading step. After the load step, dilute aqueous alcohol (2% ethanol/$H_2O$) is passed through the preparative column at the flow rate of about two bed volumes an hour to remove unbound material. Dilute aqueous alcohol effluent is discarded as a waste. After the rinse step, concentrated aqueous alcohol (20% ethanol/$H_2O$) is applied to the resin and the liquid eluate containing polyphenols is collected.

Pomegranate Dry Composition

As set forth throughout this disclosure the pomegranate fruit polyphenol extract takes the form of a dry pomegranate composition in at least one or more embodiments of the invention. This dry pomegranate composition is a lyophilized, or freeze-dried pomegranate fruit polyphenol extract. The dry pomegranate composition may also be obtained by applying heat, using desiccants, reducing pressure, applying air, or any other evaporative process capable of removing moisture, including any combination thereof.

In addition to punicalagin, other high molecular weight polyphenols characterized in the dry pomegranate composition include ellagitannin and other hydrolysable tannins, such as punicortein A, punicalin, pedunculagin, and gallotannin dimers and trimers. Once obtained the dry composition may be filled into capsules for distribution in pill form or mixed into various liquids to increase the polyphenol content of a particular liquid.

In one or more embodiments, the pomegranate dry composition is obtained from the pomegranate solid, in accordance with the methods disclosed herein. For instance, one may make use of the pericarp, inner membrane and seeds to create a mixture comprising the pomegranate solids in an aqueous solution. The mixture of the pomegranate solids may be created by adding water in an amount that is about 20 to about 80% w/v, and more preferably about 50% w/v, of the pomegranate solids. The mixture is preferably crushed or milled to create a rough grind of pomegranate solids dispersed in the aqueous solution. Once obtained the dry pomegranate composition may be filled into capsules for distribution in pill form or mixed into various liquids to increase the polyphenol content of a particular liquid.

In one or more embodiments, the dry pomegranate composition includes at least about 20-25% combined punicalin and pulicalagin by HPLC area %. Table 3 includes 3 exemplary products manufactured with different ranges of punicalagin A and punicalagin B by weight.

In one or more embodiments, the dry pomegranate composition includes less than about 5% ellagic acid and their derivatives by HPLC area %. In one or more embodiments, the dry pomegranate composition further includes less than about 4% ellagic acid and their derivatives by weight. In one or more embodiments, the dry pomegranate composition includes less than about 3% ellagic acid and their derivatives by weight.

The dry pomegranate composition further includes up to a trace amount of anthocyanins. The trace amount may be about 1% anthocyanins by weight, but depending on the method of manufacture, can less than about 0.1% anthocyanins by weight. In one or more embodiments, the trace amount of anthocyanins may be close to about 0%. Table 1 shows a product where anthocyanins were virtually undetectable using an HPLC analysis.

In one or more embodiments, the dry pomegranate composition includes at least about 85% total polyphenols. In other embodiments, the dry composition includes at least about 90% total polyphenols. In one or more embodiments, the starting materials for production of the dry pomegranate composition are solids from the husks and residual fruits that remain after the first or second pressing of whole fruits in the production of the juice concentrate. Both powder or concentrated liquid forms may be made with these materials. In one or more embodiments, the mixture of the solids may be created by adding water in an amount that is about 20 to about 80% w/v, and more preferably about 50 w/v, of the solids. The mixture may be crushed or milled to create a rough grind of pomegranate solids dispersed in the aqueous solution.

Punicalagins and other phytochemicals of pomegranate may remain stable when processed and stored in the pomegranate dry composition. Thus, a lower amount of the hydrolysable tannins, for example, in the dry composition become hydrolyzed to nonbioavailable and/or less bioactive forms. Thus one or more embodiments may be used in oral or enteral dosage form as a pharmaceutical or nutraceutical composition including, for instance, a pomegranate dry composition. This composition may be administered in oral, pill or liquid form.

The resulting liquid eluate containing polyphenols is turned into the dry pomegranate composition by employing any suitable drying methodology and apparatus. Drying can be accomplished, for example, by use of a rotary evaporator under reduced pressure and followed by further drying in a desiccator. Another example of a drying methodology is lyophilization, which comprises freezing the liquid extract and then drying the same under high vacuum conditions in order to allow the water in the solid state to sublimate at low temperature. That is, the water is removed from the material by passing directly from the solid to the gaseous state, without passing through the liquid state. One or more embodiments utilize tray drying or spray drying the liquid eluate to formulate the pomegranate fruit polyphenol extract.

In one or more embodiments, the pomegranate dry composition may be formulated in nutraceutical compositions and be delivered in an oral or enteral dosage form. Such compositions may be administered orally or enterally employing dry form preparations containing the pomegranate dry composition. The preparation of the nutraceutical composition may optionally include one or a combination of suitable binders, carriers, disintegrants, excipient, lubricants, colorants, and diluents. Such nutraceutical composition optionally comprises one or more additional coatings surrounding the core and/or the control releasing coat such as moisture barrier coats, enteric coats or coatings that affect the physical integrity and/or appearance of the nutraceutical composition.

The dosage used in the embodiments may be applied in any suitable form, such as bars, pills, capsules, gels, liquid, etc. A dosage unit may comprise a powder, solid or semisolid form, and more acceptable in a dosage form includes without limitation, caplets, capsules, gelatin coated capsule, granules, microparticles, microspheres, pills, powder, tablets, and other solid or semisolid formulations. The solid or semisolid dosage form preferably has a weight between 0.1 and 30 grams, more preferably between 0.2 and 10 grams. In the embodiments, a daily dosage of the prepared polyphenol can include one or more pills, tablets or other dosage forms. Concentrated liquid forms are also contemplated and may be made by mixing in the powder or other forms of the polyphenol composition described herein. Alternatively or in addition the liquid concentrate itself can be produced from byproducts of the juice production process.

According to at least one embodiment of the invention the enteral or oral administration of a nutraceutical composition includes the pomegranate dry composition. As mentioned concentrated liquid forms are also feasible. Particularly suitable is the administration of a dosage or serving of the nutraceutical composition containing the pomegranate dry composition. Capsule form is typically most well suited for easy consumption but all other alternatives are within the scope and spirit of the invention. The pomegranate dry composition has a substantially higher polyphenol content than other known compositions. This is particularly true with respect to the higher molecular weight polyphenols and, in particular, punicalagins. In addition to punicalagin, other high molecular weight polyphenols characterized in the pomegranate dry composition include ellagitannin and other hydrolysable tannins, such as punicortein A, punicalin, pedunculagin, and gallotannin dimers and trimers. The amount of pomegranate extract to be administered can be between about 1,000 mg to about 2,000 mg per day and anywhere in between. Dosage may exceed 2,000 mg so long as the no observed adverse effect level (NOAEL) is not exceeded. In humans the NOAEL is thought to be about 7,900 mg per day, assuming a 70 kg subject.

Dry Pomegranate Composition Analysis

An exemplary analysis of the dry pomegranate composition now follows. The pomegranate dry composition was analyzed using HPLC and MALDI-TOF. The pomegranate dry composition has a higher proportional content of pomegranate polyphenols, primarily punicalagin and its automers. Table 1 shows a composition breakdown in 100 grams of an exemplary pomegranate dry composition powder. Table 2 shows an HPLC analysis for an exemplary pomegranate fruit polyphenol composition. Table 3 shows a breakdown of specific polyphenols in three exemplary pomegranate fruit polyphenol extracts.

Once created the powder and liquid forms provide similar polyphenol components of one serving of pomegranate juice. One serving of pomegranate juice contains at least 800 mg total natural polyphenols (650 mg gallic acid equivalent, GAE) with expected variation from year to year and batch to batch. Pomegranate juice has been shown to have up to 4,370 mg/L or 1,049 mg/8 oz of punicalagin compounds by Cerda et. al., 2004. GAE underestimates the total polyphenol level because gallic acid is not optimized standard. A 1,000 mg capsule of powder made using the process described herein contains at least 800 mg natural polyphenol using a pomegranate polyphenol standard, such as but not limited to the standard described in K. Martin et al. "Development of a novel pomegranate standard and new method for the quantitative measurement of pomegranate polyphenols" Journal of Science of Food and Agriculture, 2009; 89:157-162, which is hereby incorporated by reference in its entirety. The table below is illustrative: About 1000 mg of the dry pomegranate composition and about 200 mg of maltodextrin, which is used as a flow agent, are intimately mixed for prior to filling in a capsule comprising of hydroxypropyl methylcellulose.

This amount provides the polyphenol content equivalent to an 8 oz. bottle of pomegranate juice. The purification process of Example 1 enables the requisite polyphenol dose in a single capsule.

TABLE 1

SPECIFICATIONS

| | |
|---|---|
| Chemical Classification | Organic, Nutritive |
| Physical Classification | Dried Fruit |
| Color | Red-Brown |
| Odor | Characteristic Tannin |
| Taste | Characteristic Tannin |
| Plant Part Used | Husk, Arils (Juice), and Fruit |
| Chemical Parameters | |
| Total Phenolics | >85% (UV adsorption std. to pomegranate polyphenols) |
| pH (1 g/100 ml water) | 3.0 to 5.0 |
| Heavy Metals (ppm) | Less than 1 ppm. |
| Physical Parameters | |
| Particle Size (wt. % retained on 60 mesh) | Less than 2%. |
| Bulk Density (g/cc) | 0.8 to 0.9 |
| Tap Density (g/cc) | 0.9 to 1.0 |
| Microbiological Assays: | |
| Total Plate Count (CFU/g) | <1,000 |
| Yeast (CFU/g) | <100 |
| Mold (CFU/g) | <10 |
| Total Coliforms (CFU/g) | <10 (none detected) |
| E. coli (CFU/g) | <10 (none detected) |
| Salmonella (CFU/g) | Negative in 25 grams. |
| Staph. aureus (CFU/g) | <10 (none detected) |

Shelf Life
18 months at or below 70 F in a sealed container.
Packaging
10 kg. in a double-lined plastic bag. Product should be stored in the original sealed container and tightly closed after usage.

TABLE 2

HPLC Analysis of pomegranate fruit polyphenol composition

| | HPLC % area under curve | | | Estimated polyphenol content from Folin NPPE (mg/1000 mg) | | |
|---|---|---|---|---|---|---|
| Monomeric HP Punicalin | 3.45 | 0.94 | 1.00 | 27.27 | 7.90 | 8.60 |
| Monomeric HP Punicalagin A | 5.70 | 4.75 | 4.79 | 45.02 | 39.90 | 41.19 |
| Monomeric HP Punicalagin B | 12.29 | 11.14 | 12.94 | 97.11 | 93.58 | 111.28 |
| Oligomeric HPs | 75.06 | 79.23 | 77.10 | 592.98 | 655.53 | 633.06 |
| Delphinidin 3, 5 diglucoside | 0.00 | 0.00 | 0.00 | 0.00 | 0.00 | 0.00 |
| Cyanidin 3, 5 diglucoside | 0.00 | 0.00 | 0.00 | 0.00 | 0.00 | 0.00 |
| Delphinidin 3 glucoside | 0.00 | 0.00 | 0.00 | 0.00 | 0.00 | 0.00 |
| Cyanidin 3 glucoside | 0.00 | 0.00 | 0.00 | 0.00 | 0.00 | 0.00 |
| Ellagic Acids | 3.50 | 3.94 | 4.17 | 27.63 | 33.10 | 35.86 |
| Folin Total Polyphenols | 3.50 | 3.94 | 4.17 | 27.63 | 33.10 | 35.86 |
| Group Totals | | | | 790.00 | 840.00 | 860.00 |
| HP (Hydrolysable polyphenols) | 96.50 | 96.06 | 95.83 | 762.37 | 806.90 | 824.14 |
| Anthocyanins | 0.00 | 0.00 | 0.00 | 0.00 | 0.00 | 0.00 |
| Ellagic acid aglycones | 3.50 | 3.94 | 4.17 | 27.63 | 33.10 | 35.86 |
| Non-anthocyanins (Gps 1 + 3) | 100.00 | 100.00 | 100.00 | 790.00 | 840.00 | 860.00 |
| Punicalins + Punicalagins | 21.44 | 16.83 | 18.73 | 169.40 | 141.38 | 161.07 |

TABLE 3

| Component | Method Type | Product x1 | Produt xp | Product xm |
|---|---|---|---|---|
| | | Nominal (% by weight) | | |
| Total Hydrolyzable Tannins | HPLC, UV-vis | | | |
| Gallic acid (free) | | 0.05 to 0.15 | 0.8 to 1.2 | 0.8 to 1.2 |
| Ellagic acid (free) | | 0.1 to 0.3 | 1.5 to 3.5 | 1.5 to 2.5 |
| Total Punicalagin A&B | HPLC, UV-vis | | | |
| Punicalagin A | | 0.80 to 0.95 | 1.0 to 2.0 | 5.5 to 6.5 |
| Punicalagin B | | 2.6 to 2.9 | 3.5 to 6.0 | 15 to 16 |
| Punicalagin A & B | | 3.0 to 4.0 | 4.5 to 8.0 | 20 to 22 |

What is claimed is:

1. A pharmaceutical composition comprising:
a capsule body;
a composition within said capsule body, wherein said composition comprises
a pomegranate fruit polyphenol extract obtained from pomegranate solids comprising pericarp, inner membrane, and seeds, wherein said pomegranate fruit polyphenol extract comprises
at least 3% combined punicalagin A and punicalagin B by weight,
less than 5% ellagic acid by weight, and
less than 1% anthocyanins by weight; and
a capsule cap secured onto said capsule body thereby encapsulating said composition within a capsule formed by bonding said capsule cap to said capsule body.

2. The pharmaceutical composition of claim 1, wherein said pomegranate fruit polyphenol extract comprises between about 3% to about 8% combined punicalagin A and punicalagin B by weight.

3. The pharmaceutical composition of claim 1, wherein said pomegranate fruit polyphenol extract comprises at least 4.5% combined punicalagin A and punicalagin B by weight.

4. The pharmaceutical composition of claim 1, wherein said pomegranate fruit polyphenol extract comprises at least about 20% combined punicalagin A and punicalagin B by weight.

5. The pharmaceutical composition of claim 1, wherein said pomegranate fruit polyphenol extract comprises at least about 15% combined punicalagin and punicalin by weight.

6. The pharmaceutical composition of claim 1, wherein said pomegranate fruit polyphenol extract comprises at least about 25% combined punicalagin and punicalin by weight.

7. The pharmaceutical composition of claim 1, wherein said pomegranate fruit polyphenol extract comprises less than about 4% ellagic acid by weight.

8. The pharmaceutical composition of claim 1, wherein said pomegranate fruit polyphenol extract comprises less than about 1.5% free ellagic acid.

9. The pharmaceutical composition of claim 1, wherein said pomegranate fruit polyphenol extract comprises less than about 0.3% free ellagic acid.

10. The pharmaceutical composition of claim 1, wherein said composition further comprises a pharmaceutically acceptable carrier.

11. The pharmaceutical composition of claim 1, wherein said pomegranate fruit polyphenol extract comprises less than about 0.1% anthocyanins by weight.

12. The pharmaceutical composition of claim 1, wherein said pomegranate fruit polyphenol extract comprises at least about 1000 mg in a dry composition.

13. The pharmaceutical composition of claim 12, wherein said dry composition comprises at least about 80% total polyphenols.

14. The pharmaceutical composition of claim 12, wherein said dry composition comprises at least about 90% total polyphenols.

15. The pharmaceutical composition of claim 1, wherein the pharmaceutical composition is selected from an immediate release composition, a delayed release composition, an extended release composition, a mixed release composition and an enterically coated composition.

16. A pharmaceutical composition comprising:
a capsule body;
a composition within said capsule body, wherein said composition comprises a pomegranate fruit polyphenol extract obtained from pomegranate solids comprising pericarp, inner membrane, and seeds, wherein said pomegranate fruit polyphenol extract comprises at least 3% combined punicalagin A and punicalagin B by weight, less than 5% ellagic acid by weight, and less than 1% anthocyanins by weight;
a pharmaceutically suitable carrier within said capsule body; and
a capsule cap secured onto said capsule body thereby encapsulating said composition and said pharmaceutically suitable carrier within a capsule formed by bonding said capsule cap to said capsule body.

* * * * *